US005733337A

United States Patent [19]

Carr, Jr. et al.

[11] Patent Number: 5,733,337
[45] Date of Patent: Mar. 31, 1998

[54] TISSUE REPAIR FABRIC

[75] Inventors: Robert M. Carr, Jr., West Roxbury, Mass.; Paul L. Termin, St. Paul, Minn.; Kimberlie D. Condon, Brant Rock, Mass.

[73] Assignee: Organogenesis, Inc., Canton, Mass.

[21] Appl. No.: 417,868

[22] Filed: Apr. 7, 1995

[51] Int. Cl.$^6$ .................................................. A61F 2/06
[52] U.S. Cl. ............................ 623/11; 623/1; 623/12; 606/194; 606/213; 606/214; 530/356
[58] Field of Search .................... 623/1, 11, 12, 623/66, 8, 13, 15, 16; 606/194, 213, 214; 530/356

[56] References Cited

U.S. PATENT DOCUMENTS

| | | |
|---|---|---|
| 3,562,820 | 2/1971 | Braun . |
| 4,503,159 | 3/1985 | Woodroof . |
| 4,787,900 | 11/1988 | Yannas ........................................ 623/1 |
| 4,801,299 | 1/1989 | Brendel . |
| 4,822,361 | 4/1989 | Okita et al. ............................ 623/12 |
| 4,902,289 | 2/1990 | Yannas . |
| 4,902,508 | 2/1990 | Badylak . |
| 4,956,178 | 9/1990 | Badylak et al. ...................... 424/551 |
| 5,061,276 | 10/1991 | Tu et al. .................................. 623/1 |
| 5,256,418 | 10/1993 | Kemp . |
| 5,263,983 | 11/1993 | Yoshizato et al. ...................... 623/12 |
| 5,281,422 | 1/1994 | Badylak . |
| 5,372,821 | 12/1994 | Badylak . |
| 5,378,469 | 1/1995 | Kemp et al. .......................... 424/423 |
| 5,460,962 | 10/1995 | Kemp ..................................... 435/238 |
| 5,571,216 | 11/1996 | Anderson ............................... 623/66 |

FOREIGN PATENT DOCUMENTS

| | | |
|---|---|---|
| 0493788 | 7/1992 | European Pat. Off. . |
| 0493788 | 8/1992 | European Pat. Off. . |

OTHER PUBLICATIONS

Webster's II New Riverside University Dictionary, pp. 388, 1212, Copyright 1984, 1988, 1994 Houghton, Mifflin Company, 1984.
Lawler, et al., The Amer. J. of Surgery, vol. 12 (Oct.) pp. 517–519 (1971).
Dagan, et al., Vascular Surgery (Jul./Aug. 1983), pp. 199–206.
Egusa S., Acta Md. Okayama vol. 22, pp. 153–165 (1968).
Fraser, et al. (1968) Arch. Surg. vol. 96 (Mar.) pp. 378–385.
Broll, et al., (1968) Eur. Surg. Res. vol 18, pp. 390–396.
Wyler, et al. (1992), Journal of Biomedical Materials Research, vol. 26 pp. 1141–1146.
Hiles, M.C., et al., (Feb. 1993) Journal of Biomedical Material Research, vol. 27, pp. 139–144.
Matsumoto, T., et al., Surgery (1966) vol. 603, pp. 739–743.

*Primary Examiner*—John G. Weiss
*Assistant Examiner*—Francis K. Cuddihy
*Attorney, Agent, or Firm*—Hale and Dorr LLP

[57] ABSTRACT

This invention is directed to prosthesis, which, when implanted into a mammalian patient, serve as a functioning replacement for a body part, or tissue structure, and will undergo controlled biodegradation occurring concomitantly with bioremodeling by the patient's living cells. The prosthesis of this invention, in its various embodiments, thus has dual properties. First, it functions as a substitute body part, and second, it functions as bioremodeling template for the ingrowth of host cells.

24 Claims, No Drawings

TISSUE REPAIR FABRIC

FIELD OF THE INVENTION

This invention is in the field of implantable biological prostheses. The present invention is a resilient, biocompatible two or more layered tissue prosthesis which can be engineered into a variety of shapes and used to repair, augment, or replace mammalian tissues and organs. The prosthesis is gradually degraded and remodeled by the host's cells which replace the implanted prosthesis to restore structure and function.

BACKGROUND OF THE INVENTION

Despite the growing sophistication of medical technology, repairing and replacing damaged tissues remains a frequent, costly, and serious problem in health care. Currently implantable prosthesis are made from a number of synthetic and treated natural materials. The ideal prosthetic material should be chemically inert, noncarcinogenic, capable of resisting mechanical stress, capable of being fabricated in the form required, and sterilizable, yet not be physically modified by tissue fluids, excite an inflammatory or foreign body reaction, induce a state of allergy or hypersensitivity, or promote visceral adhesions (Jenkins SD, et al. *Surgery* 94(2):392–398, 1983).

For example, body wall defects that cannot be closed with autogenous tissue due to trauma, necrosis or other causes require repair, augmentation, or replacement with synthetic mesh. In reinforcing or repairing abdominal wall defects, several prosthetic materials have been used, including tantalum gauze, stainless steel mesh, DACRON®, ORLON®, FORTISAN®, nylon, knitted polypropylene (MARLEX®), microporous expanded-polytetrafluoroethylene (GORE-TEX®), dacron reinforced silicone rubber (SILASTIC®), polyglactin 910 (VICRYL®), polyester (MERSILENE®), polyglycolic add (DEXON®), processed sheep dermal collagen (PSDC®), crosslinked bovine pericardium (PERI-GUARD®), and preserved human dura (LYODURA®). No single prosthetic material has gained universal acceptance.

The major advantages of metallic meshes are that they are inert, resistant to infection and can stimulate fibroplasia. Their major disadvantage is the fragmentation that occurs after the first year of implantation as well as the lack of malleability. Synthetic meshes have the advantage of being easily molded and, except for nylon, retain their tensile strength in the body. Their major disadvantage is their lack of inertness to infection and their interference with wound healing.

Absorbable meshes have the advantage of facilitating tissue ingrowth and remodeling at the site of implantation, but often have the disadvantage of losing their mechanical strength, because of dissolution by the host, prior to adequate tissue ingrowth.

The most widely used material for abdominal wall replacement and for reinforcement during hernia repairs is MARLEX®, however, several investigators reported that with scar contracture, polypropylene mesh grafts became distorted and separated from surrounding normal tissue in a whorl of fibrous tissue. Others have reported moderate to severe adhesions when using MARLEX®.

GORE-TEX® is currently believed to be the most chemically inert polymer and has been found to cause minimal foreign body reaction when implanted. A major problem exists with the use of polytetrafluoroethylene in a contaminated wound as it does not allow for any macromolecular drainage, which limits treatment of infections.

Processed dermal sheep collagen has been studied as an implant for a variety of applications. Before implantation, the sheep dermal collagen is typically tanned with hexamethylenediisocyanate (PB van Wachem, et al. *Biomaterials* 12(March):215–223, 1991) or glutaraldehyde (V. J. Rudolphy, et al. *Ann Thorac Surg* 52:821–825, 1991)

It is a continuing goal of researchers to develop implantable prostheses which can successfully be used to replace or repair mammalian tissue, such as abdominal wall defects.

SUMMARY OF THE INVENTION

The present invention overcomes the difficulties of the materials currently available and provides a prosthetic device for use in the repair, augmentation, or replacement of damaged tissues and organs. This invention is directed to a prosthesis, which, when implanted into a mammalian host, undergoes controlled biodegradation accompanied by adequate living cell replacement, or neo-tissue formation, such that the original implanted prosthesis is remodeled by the host's cells before it is degraded by host enzymes. The prosthesis of this invention, a tissue repair fabric, comprises at least two layers of superimposed, bonded collagen material. The bonded collagen layers of the invention are structurally stable, pliable, semi-permeable, and suturable.

It is, therefore, an object of this invention to provide a tissue repair fabric that does not exhibit many of the shortcomings associated with many of the grafts now being used clinically.

Another object is the provision of a prosthesis that will allow for and facilitate tissue ingrowth and/or organ regeneration at the site of implantation.

A further object of the current invention is to provide a simple, repeatable method for manufacturing a tissue repair fabric.

Still another object of this invention is to provide a method for use of a novel multi-purpose tissue repair fabric in autografting, allografting, and heterografting indications.

Still a further object is to provide a novel tissue repair fabric that Can be implanted using conventional surgical techniques.

DETAILED DESCRIPTION OF THE INVENTION

This invention is directed to a tissue engineered prostheses, which, when implanted into a mammalian host, can serve as a functioning repair, augmentation, or replacement for a body part, or tissue structure, and will undergo controlled biodegradation occurring concomitantly with remodeling by the host's cells. The prosthesis of this invention, in its various embodiments, thus has dual properties: First, it functions as a substitute body part and second, while still functioning as a substitute body part, it functions as a remodeling template for the ingrowth of host cells. The prosthesis of this invention, a tissue repair fabric, comprises at least two layers of superimposed, bonded collagen material. Although, the prostheses will be illustrated through construction of various devices, the invention is not so limited. It will be appreciated that the device design in its shape and thickness is to be selected depending on the ultimate indication for the construct.

In the preferred embodiment, collagenons tissues from the mammalian body are used to make said collagen layer. Collagenous tissue sources include, but are not limited to, the intestine, fascia lata, pericardium, and dura mater. The most preferred material for use is the tunica submucosa layer of the small intestine. The tunica submucosa may be separated, or delaminated, from the other layers of the small intestine. This layer is referred to hereinafter as the Intestinal Collagen Layer ("ICL"). Further, the collagen layers of the prosthetic device may be from the same collagen material, such as two or more layers of ICL, or from different collagen materials, such as one or more layers of ICL and one or more layers of facia lata.

The submucosa, or the intestinal collagen layer (ICL), from a mammalian source, typically pigs, cows, or sheep, is mechanically cleaned by squeezing the raw material between opposing rollers to remove the muscular layers (tunica muscularis) and the mucosa (tunica mucosa). The tunica submucosa of the small intestine is harder and stiffer than the surrounding tissue, and the rollers squeeze the softer components from the submucosa. In the examples that follow, the ICL was mechanically harvested from the small intestine of a porcine using a Bitterling sausage casing machine.

As the mechanically cleaned submucosa may have some hidden, visibly nonapparent debris that affects the consistency of the mechanical properties, the submucosa may be chemically cleaned to remove debris and other substances, other than collagen, for example, by soaking in buffer solutions at 4° C., without the use of any detergents such as Triton or SDS, or by soaking with NaOH or trypsin, or other known cleaning techniques.

After cleaning, the (ICL) should be decontaminated, preferably with the use of dilute peracetic acid solutions as described in U.S. Pat. No. 5,460,962, incorporated herein by reference. Other sterilization systems for use with collagen are known in the art and can be used. The prosthetic device of this invention has two or more collagen layers that are bonded together. As used herein "bonded collagen layers" mean composed of two or more layers of the same or different collagen material treated in a manner such that the layers are superimposed on each other and are sufficiently held together by self-lamination. The bonding of the collagen layers may be accomplished in a number of different ways: by heat welding, adhesives, chemical linking, or sutures.

In the preferred method, and in the examples that follow, the ICL was disinfected with 0.05% peracetic acid and stored until use at 4° C. in sterile phosphate buffered saline (PBS). The ICL is cut longitudinally and flattened onto a solid, flat plate. One or more successive layers are then superimposed onto one another. A second solid flat plate is placed on top of the layers and the two plates are clamped tightly together. The complete apparatus, clamped plates and collagen layers, are then heated for a time and under conditions sufficient to effect the bonding of the collagen layers together. The amount of heat applied should be sufficiently high to allow the collagen to bond, but not so high as to cause the collagen to completely denature. The heat will typically cause some amount of minor denaturation, which will be adhesion areas in the self lamination of the collagen layers. The time of the heating and bonding will depend upon the type of collagen material layer used, the thickness of the material, and the applied heat. A typical range of heat is from about 50° C. to about 75° C., more typically 60° C. to 65° C. and most typically 62° C. A typical range of times will be from about 7 minutes to about 24 hours, typically about one hour. The degree of heat and the amount of time that the heat is applied can be readily ascertained through routine experimentation of varying the heat and time parameters. The bonding step may be accomplished in a conventional oven, although other apparatus or heat applications may be used including, but not limited to, a water bath, laser energy, or electrical heat conduction. Immediately following the heating and bonding, the apparatus is cooled, in air or a water bath, at a range between room temperature at 20° C. and 1° C. Rapid cooling, termed quenching, will immediately, or almost immediately, stop the heating action. To accomplish this step, the apparatus may be cooled, typically in a water bath, with a temperature preferably between about 1° C. to about 10° C., most preferably about 4° C. Although cooling temperatures below 1° C. may be used, care will need to be taken not to freeze the collagen layers, which may cause structural damage. In addition, temperatures above 10° C. may be used in quenching, but if the temperature of the quench is too high, then the heating may not be stopped in time to sufficiently fix the collagen layers in their current configuration.

The multi-layered construct is preferably then crosslinked. Crosslinking the bonded prosthetic device provides strength and some durability to the device to improve handling properties. Crosslinking agents should be selected so as to produce a biocompatible material capable of being remodeled by host cells. Various types of crosslinking agents are known in the art and can be used such as acyl-azide, ribose and other sugars, oxidative agents and dehydrothermal (DHT) methods. A preferred crosslinking agent is 1-ethyl-3-(3-dimethylaminopropyl) carbodiimide hydrochloride (EDC). The crosslinking solution containing EDC and water may also contain acetone. In a preferred embodiment, sulfo-N-hydroxysuccinimide is added to the crosslinking agent (Staros, 1982). There are certain crosslinking agents that cannot be used on the prosthesis of this invention since they will produce a crosslinked material that will not undergo remodeling by host cells. Glutaraldehyde, for example, is not a preferred agent for crosslinking with this invention as the residual of the glutaraldehyde monomer and lower molecular polymers are cytotoxic. Therefore, it would prevent cell ingrowth and bioremodeling.

The finished collagen prosthetic device when properly bonded should have the following characteristics: Uniform thickness, homogenous texture, non-porous, suturable and non-immunogenic.

The tissue repair fabric of this invention, functioning as a substitute body part, may be flat, tubular, or of complex geometry. The shape of the tissue repair fabric will be decided by its intended use. Thus, when forming the bonding layers of the prosthesis of this invention, the mold or plate can be fashioned to accommodate the desired shape. The tissue repair fabric can be implanted to repair, augment, or replace diseased or damaged organs, such as abdominal wall defects, pericardium, hernias, and various other organs and structures including, but not limited to, bone, periosteum, perichondrium, intervertebral disc, articular cartilage, dermis, epidermis, bowel, ligaments, and tendons. In addition, the tissue repair fabric can be used as a vascular or intra-cardiac patch, or as a replacement heart valve.

Flat sheets may be used, for example, to support prolapsed or hypermobile organs by using the sheet as a sling for the organs. This sling can support organs such as bladder or uterus.

Tubular grafts may be used, for example, to replace cross sections of tubular organs such as esophagus, trachea, intestine, and fallopian tubes. These organs have a basic tubuilar shape with an outer surface and a luminal surface.

In addition, flat sheets and tubular structures can be formed together to form a complex structure to replace or augment cardiac or venous valves.

In addition to functioning as a substitute body part or support, the second function of the prosthesis is that of a template for bioremodeling. "Bioremodeling" is used herein to mean the production of structural collagen, vascularization, and epithelialization by the ingrowth of host cells at a rate faster than the loss of mechanical strength of the implanted prosthesis due to biodegradation by host enzymes. The tissue repair fabric retains the characteristics of the originally implanted prosthesis while it is remodeled by the host into all, or substantially all, host tissue, and as such, is functional as a tissue structure.

The mechanical properties include mechanical integrity such that the tissue repair fabric resists creep during bioremodeling, and additionally is pliable and suturable. The term "pliable" means good handling properties. The term "suturable" means that the mechanical properties of the layer include suture retention which permits needles and suture materials to pass through the prosthesis material at the time of suturing of the prosthesis to sections of native tissue, a process known as anastomosis. During suturing, such prostheses must not tear as a result of the tensile forces applied to them by the suture, nor should they tear when the suture is knotted. Suturability of tissue repair fabric, i.e., the ability of prostheses to resist tearing while being sutured, is related to the intrinsic mechanical strength of the prosthesis material, the thickness of the graft, the tension applied to the suture, and the rate at which the knot is pulled closed.

As used herein, the term "non-creeping" means that the biomechanical properties of the prosthesis impart durability so that the prosthesis is not stretched, distended, or expanded beyond normal limits after implantation. As is described below, total stretch of the implanted prosthesis of this invention is within acceptable limits. The prosthesis of this invention acquires a resistance to stretching as a function of post-implantation cellular bioremodeling by replacement of structural collagen by host cells at a faster rate than the loss of mechanical strength of the implanted materials due from biodegradation and remodeling. The tissue repair fabric of the present invention is "semi-permeable," even though it has been crosslinked. Semi-permeability permits the ingrowth of host cells for remodeling or for deposition of the collagenous layer. The "non-porous" quality of the prosthesis prevents the passage of fluids that are intended to be retained by the implantation of the prosthesis. Conversely, pores may be formed in the prosthesis if the quality is required for an application of the prosthesis.

The mechanical integrity of the prosthesis of this invention is also in its ability to be draped or folded, as well as the ability to cut or trim the prosthesis obtaining a clean edge without delaminating or fraying the edges of the construct.

Additionally, in another embodiment of the invention, mechanically sheared or chopped collagen fibers can be included between the collagen layers adding bulk to the construct and providing a mechanism for a differential rate of remodeling by host cells. The properties of the construct incorporating the fibers may be altered by variations in the length and diameter of the fibers; variations on the proportion of the fibers used, and fully or partially crosslinking fibers. The length of the fibers can range from 0.1 cm to 5.0 cm.

In another embodiment of the invention, collagen threads are incorporated into the multilayered tissue repair fabric for reinforcement or for different rates of remodeling. For example, a helix or "twist", of a braid of 20 to 200 denier collagen thread may be applied to the surface of the tissue repair fabric. The diameter size of the helix or braid of collagen thread can range from 50 to 500 microns, preferably 100 to 200 microns. Thus, the properties of the tissue repair fabric layer can be varied by the geometry of the thread used for the reinforcement. The functionality of the design will be dependent on the geometry of the braid or twist. Additionally, collagen thread constructs such as a felt, a flat knitted or woven fabric, or a three-dimensional knitted, woven or braided fabric may be incorporated between the layers or on the surface of the construct. Some embodiments may also include a collagen gel between the layers alone or with a drug, growth factor or antibiotic to function as a delivery system. Additionally, a collagen gel could be incorporated with a thread or a thread construct between the layers.

As will be appreciated by those of skill in the art, many of the embodiments incorporating collagen gel, thread or a thread construct will also effect the physical properties, such as compliance, radial strength, kink resistance, suture retention, and pliability. Physical properties of the thread or the thread construct may also be varied by crosslinking the threads.

In some embodiments, additional collagenons layers may be added to the outer or inner surfaces of the bonded collagen layers to create a smooth flow surface for its ultimate application as described in International PCT Publication No. WO 95/22301, the contents of which are incorporated herein by reference. This smooth collagenons layer also promotes host cell attachment which facilitates ingrowth and bioremodeling. As described in International PCT Publication No. WO 95/22301, this smooth collagenons layer may be made from acid-extracted fibrillar or non-fibrillar collagen, which is predominantly type I collagen, but may also include type III collagen, type IV collagen, or both. The collagen used may be derived from any number of mammalian sources, typically bovine, porcine, or ovine skin and tendons. The collagen preferably has been processed by acid extraction to result in a fibril dispersion or gel of high purity. Collagen may be acid-extracted from the collagen source using a weak acid, such as acetic, citric, or formic acid. Once extracted into solution, the collagen can be salt-precipitated using NaCl and recovered, using standard techniques such as centrifugation or filtration. Details of acid extracted collagen are described, for example, in U.S. Pat. No. 5,106,949, incorporated herein by reference.

Collagen dispersions or gels for use in the present invention are generally at a concentration of about 1 to 10 mg/ml, preferably, more about 2 to 6 mg/ml, and most preferably at about 2 to 4 mg/ml and at pH of about 2 to 4. A preferred solvent for the collagen is dilute acetic acid, e.g., about 0.05 to 0.1%. Other conventional solvents for collagen may be used as long as such solvents are compatible.

Once the prosthetic device has been produced, it may be air dried, packaged, and sterilized with gamma irradiation, typically 2.5 Mrad, and stored.

In the examples that follow, the ICL is cut longitudinally and flattened out onto a glass plate, although any inert non-insulated firm mold may be used. In addition, the mold can be any shape: flat, rounded, or complex. In a rounded or complex mold, the bottom and upper mold pieces will be appropriately constructed so as to form the completed prosthesis into the desired shape. Once so constructed, the prosthesis will keep its shape. Thus, for example, if the prosthesis is formed into a rounded shape, it can be used as a heart valve leaflet replacement.

The multi-layered tissue repair fabric may be tubulated by various alternative means or combinations thereof. The multilayered tissue repair fabric may be formed into a tube in either the normal or the everted position, but the everted position is preferred. The tube may be made mechanically by suturing, using alternating knot stitches with suitable suture material. The knot stitch is advantageous as it allows the tube to be trimmed and shaped by the surgeon at the time of implantation without unraveling. Other processes to seam the submucosa may include adhesive bonding, such as the use of fibrin-based glues or industrial-type adhesives such as polyurethane, vinyl acetate or polyepoxy. Heat bonding techniques may also be used including heat welding or laser welding of the seam, followed by quenching, to seal the sides of the thus formed tube. Other mechanical means are possible, such as using pop rivets or staples. With these tubulation techniques, the ends of the sides may be either butt ended or overlapped. If the sides are overlapped, the seam may be trimmed once the tube is formed. In addition, these tubulation techniques are typically done on a mandrel so as to determine the desired diameter.

The thus formed structural tube can be kept on a mandrel or other suitable spindle for further processing. To control the biodegradation rates and therefore the rate of prosthesis strength decrease during bioremodeling, the prosthesis is preferably crosslinked, using a suitable crosslinking agent, such as 1-ethyl-3-(3-dimethylaminopropyl) carbodiimide hydrochloride (EDC). Crosslinking the prosthesis also aids in preventing luminal creep, in keeping the tube diameter uniform, and in increasing the burst strength. It is believed that crosslinking the intestinal collagen layer also improves the suture retention strength by improving resistance to crack propagation.

Collagen may be deposited on the internal or external surface of the ICL as described in Example 5 of U.S. Pat. No. 5,256,418, incorporated herein by reference. Briefly, when the tissue repair fabric is to be tubulated, the multi-layered fabric is fitted at one end by luer fittings and the collagen dispersion fills the tube. This step may also be accomplished as described in the above-referenced patent application using a hydrostatic pressure head. The inner layer of collagen can also be deposited by flowing collagen into both ends of the tube simultaneously. The tube is then placed into a bath of 20% polyethylene glycol (PEG) in isotonic phosphate buffered saline (PBS), neutral pH. The osmotic gradient between the internal collagen solution and outer PEG solution in combination cause a simultaneous concentration and deposition of the collagen along the lumen of the internal structural layer wall. The tube is then removed from the PEG bath, and a glass rod with a diameter desired diameter of the prosthesis lumen is inserted into the collagen solution. The prosthesis is then allowed to dry. The tube is then rehydrated in PBS. This process allows the collagenous layer to fill slight irregularities in the intestinal structural layer, thus resulting in a prosthesis of uniform thickness. The procedure also facilitates the bonding of the collagen gel to the intestinal collagen layer. A collagenous layer of varying thickness and density can be produced by changing the deposition conditions which can be determined by routine parameter changes. The same procedures can be used to apply the collagen to the outer surface of the ICL to create a three-layer prosthesis.

The prosthesis construct is thrombogenic in small diameter blood vessel replacements. It can only be used in vascular applications in high flow (large diameter) vessels. Therefore, the prosthesis must be rendered non-thrombogenic if to be useful for small diameter blood vessel repair or replacement.

Heparin can be applied to the prosthesis, by a variety of well-known techniques. For illustration, heparin can be applied to the prosthesis in the following three ways. First, benzalkonium heparin (BA-Hep) solution can be applied to the prosthesis by dipping the prosthesis in the solution and then air-drying it. This procedure treats the collagen with an ionically bound BA-Hep complex. Second, EDC can be used to activate the heparin, then to covalently bond the heparin to the collagen fiber. Third, EDC can be used to activate the collagen, then covalently bond protamine to the collagen and then ionically bond heparin to the protamine. Many other coating, bonding, and attachment procedures are well known in the art which could also be used.

Treatment of the tissue repair fabric with drugs in addition to or in substitution for heparin may be accomplished. The drugs may include for example, growth factors to promote vascularization and epithelialization, such as macrophage derived growth factor (MDGF), platelet derived growth factor (PDGF), endothelial cell derived growth factor (ECDGF); antibiotics to fight any potential infection from the surgery implant; or nerve growth factors incorporated into the inner collagenous layer when the prosthesis is used as a conduit for nerve regeneration. In addition to or in substitution for drugs, matrix components such as proteoglycans or glycoproteins or glycosaminoglycans may be included within the construct.

The tissue repair fabric can be laser drilled to create micron sized pores through the completed prosthesis for aid in cell ingrowth using an excimer laser (e.g. at KrF or ArF wavelengths). The pore size can vary from 10 to 500 microns, but is preferably from about 15 to 50 microns and spacing can vary, but about 500 microns on center is preferred. The tissue repair fabric can be laser drilled at any time during the process to make the prosthesis, but is preferably done before decontamination or sterilization.

Voids or spaces can also be formed by the method of phase inversion. At the time of layering the ICL, between layers is distributed crystalline particles that are insoluble in the liquid heat source for bonding but should be soluble in the quench bath or the crosslinking solution. If laser or dry heat is used to bond the layers then any soluble crystalline solid may be used as long as it is soluble in the quench bath or the crosslinking solution. When the crystalline solid is solubilized and has diffused out, there remains a space in which the solid had occupied. The size of the particles may vary from 10 to 100 microns, but is preferably from about 15 to 50 microns and spacing can vary between particles when distributed between the layers. The number and size of the voids formed will also effect the physical properties (i.e., compliance, kink resistance, suture retention, pliability).

The following examples are provided to better elucidate the practice of the present invention and should not be interpreted in any way to limit the scope of the present invention. Those skilled in the art will recognize that various modifications, can be made to the methods described herein while not departing from the spirit and scope of the present invention.

EXAMPLES

Example 1

Harvesting and Processing of The Intestinal Collagen Layer from Porcine Intestine The small intestine of a pig was harvested and mechanically stripped, using a Bitterling sausage casing machine which mechanically removes the tissue layers from the tunica submucosa using a combination of mechanical action and washing using hot water. The mechanical action can be described as a series of rollers that compress and strip away the successive layers from the tunica submucosa when the intact intestine is run between them. The tunica submucosa of the small intestine is harder and stiffer than the surrounding tissue, and the rollers squeeze the softer components from the submucosa. The result of the machine cleaning was such that the submucosal layer of the intestine solely remained. Finally, the submucosa was decontaminated or sterilized with 0.3% peracetic acid for 18 hours at 4° C. and then washed in phosphate buffered saline. The product that remained was an intestinal collagen layer (ICL).

Example 2

Various Welding Temperatures and EDC Concentrations of ICL

The effects of welding temperature (followed by quenching), weld time, 1-ethyl-3-(3-(dimethylamino) propyl)carbodiimide (EDC) concentration, acetone concentration and crosslinking time, after welding on weld strength were examined for the ICL two layered tube application. ICL was porcine derived as described in the Example 1. Strength qualifies were measured using a suture retention test and a ultimate tensile strength (UTS) test.

ICL was inverted and stretched over a pair of mandrels which were inserted into an ICL mounting frame. Mandrels were of stainless steel tubing with an external diameter of 4.75 mm. The ICL and mandrels were then placed in a dehydration chamber set at 20% relative humidity at 4° C. for about 60 minutes. After dehydration, the ICL was removed from the chamber and the mandrels. The lymphatic tag areas were removed and the ICL was manually wrapped around the mandrel twice to form an 'unwelded' bilayer construct. The wrapped ICL was returned to the dehydration chamber and allowed to dry for another 90 minutes still at 20% relative humidity to about 50% moisture +/−10%. To determine the amount of moisture present in a sample construct, a CEM™ oven was used.

A THERMOCENTER™ oven was set for the designated temperature treatment for the constructs to be welded. Temperatures tested for welding ranged from 55° to 70° C. Once the constructs were placed in the oven, the oven was allowed to equilibrate before timing began. The constructs were allowed to remain in the chamber for the time required for that condition. Welding times ranged from 7 to 30 minutes. As soon as the time was completed the constructs were removed from the chamber and placed in a 4° C. water bath for about 2 to 5 minutes. The welded constructs were then returned to the dehydration chamber for about 30 minutes until dehydrated to about 20% +/−10%.

After dehydration, constructs were inserted into a vessel containing EDC in either deionized water or deionized water and acetone at the concentrations appropriate for the conditions tested. EDC concentrations tested were 50, 100, and 200 mM. Acetone concentrations tested were 0, 50, and 90% in water. The time duration for crosslinking was determined by the conditions tested. Crosslinking times were 6, 12, and 24 hours. After crosslinking, the construct was removed from the solution and rinsed with physiological pH phosphate buffered saline (PBS) three times at room temperature. The welded and crosslinked construct was then removed from the mandrel and stored in PBS until testing. In addition to the thirty constructs that were prepared, two other bilayer constructs were prepared by welding at 62° C. for 15 minutes and crosslinked in 100 mM EDC in 100% $H_2O$ for 18 hours.

The suture retention test was used to determine the ability of a construct to hold a suture. A piece of construct was secured in a CHATTILION™ force measurement device and 1–2 mm bite was taken with a SURGILENE™ 6-0 suture, pulled through one wall of the construct and secured. The device then pulls at the suture to determine the force required to tear the construct material. The average suture breaks between 400–500 g of force; the surgeons pull tends to be 150 g of force.

The weld/material strength test was performed to determine the UTS of a construct. Sample rings of 5 mm lengths were excised from each tube and each was tested for their ultimate tensile strength (UTS) test using a mechanical testing system MTS™. Three sample rings were excised from each tube for three test pulls done for each construct for a total of 90 pulls. A ring was placed in the grips of the MTS™ and is pulled at a rate of 0.02 $kg_{force}$/sec until the weld slips or breaks, or until the material (rather than the weld) breaks.

Example 3

Various Welding Temperatures of ICL

The effect of welding temperature and quenching after welding on weld strength were examined for the ICL two layered tube application.

An ICL sample of 10 feet long was cut along its length and prepared as in the procedure outlined in Example 2. Six 6 mm diameter tubes ranging between 15–20 cm in length were prepared for each temperature condition.

Tubes were subjected to a temperature condition while wet for 3.5 hours. Temperatures conditions were: room temperature (20° C.), 55° C., 62° C. and 62° C. then immediately quenched in 4° C. bath for one minute. All tubes were then crosslinked in EDC. Six tubes were placed together in 300 mL 100 mM EDC overnight at room temperature. Tubes were then rinsed with physiological strength phosphate buffered saline after crosslinking.

Sample rings of 5 mm lengths were excised from each tube and each was tested for ultimate tensile strength (UTS) test using a MTS™. Five sample rings were taken from each tube for 5 test pulls on each of 6 tubes per condition for a total of 30 pulls.

Weld strength was less consistent for tubes 'welded' at room temperature as compared to the other temperature treatments when tested using the UTS test. One of the six tubes welded at room temperature had UTS measurements comparable to those of the other treatments. For the tubes welded at other temperatures either with or without quenching, there were no differences in weld strength. After UTS testing, it was determined that the breaking of the material was not a separation of the weld but a material failure in all instances.

Example 4

The Antigenicity of Crosslinked Intestinal Collagen Layer

Fresh samples of porcine submucosal intestinal layer were obtained after the cleaning step as described in example 1. Samples were then left untreated and stored in water, soaked in physiological strength phosphate buffered saline, treated with 0.1% peracetic acid, or were treated with 0.1% peracetic acid and then additionally crosslinked with 1-ethyl-3-(3-dimethylaminopropyl) carbodiimide hydrochloride (EDC). Samples were then extracted with a solution of 0.5M NaCl/0.1M tartaric acid for about 18 hours.

Two 12% Tris-glycine sodium dodecylsulfate-polyacrylamide gels (Novex Precast Gels cat #EC6009) were run and then transferred after about 18 hours to 0.45 µ nitrocellulose paper. Tartaric acid extracts of either untreated or treated ICL were run against a control standard lane containing: 10 µl Kaleidoscope Prestained Standards (Bio-Rad cat#161-0324); 2 µl biotinylated SDS-PAGE low range molecular weight standards (Bio-Rad cat# 161-0306): 6 µl loading buffer; 10 µl of control standard were loaded to each lane. The gel was blotted for about 2 hours with 1% dry non-fat milk (Carnation) in phosphate buffered saline. The gel was then washed three times with borate buffered saline/Tween with 200 µl of wash per lane. Primary antibody in 200 µl of Rb serum and borate buffered saline (100 mM boric acid : 25 mM sodium borate: 150 mM NaCl)/Tween was added to each lane at various titer range (1:40, 1:160, 1:640 and 1:2560). The gel was then incubated at room temperature for one hour on a rocker platform (Bellco Biotechnology) with the speed set at 10. The gel was then washed again three times with borate buffered saline/Tween. Secondary antibody, goat anti-rabbit Ig-AP (Southern Biotechnology Associates Inc. cat#4010-04) at a 1:1000 dilution was added to lanes at 200 µl per lane and the gel was incubated for one hour at room temperature on a rocker platform. The nitrocellulose membrane was then immersed in AP color development solution while incubated at room temperature on a rocker platform until color development was complete. Development was stopped by washing the membrane in dionized water for ten minutes on a rocker platform while changing the water once during the ten minutes. The membrane was then air dried.

Nitrocellulose gel development showed that peracetic acid treated/EDC crosslinked ICL has similar banding as demonstrated by the sham sample while non treated ICL and peracetic acid (not EDC) treated ICL showed intense banding. The results obtained suggest that the antigenicity of the porcine derived ICL treated with peracetic acid and EDC has greatly reduced antigenicity as compared to the other treatments.

Example 5

Six Layered Tissue Repair Fabric as an Abdominal Wall Patch

Six layers of porcine intestinal collagen were superimposed onto one another on a glass plate. A second plate of glass was then placed on top of the intestinal collagen layers and clamped tightly to the first plate. The apparatus was placed into a conventional type oven at 62° C. for one hour. Immediately following heating, the apparatus was placed into a 4° C. water bath for ten minutes. The apparatus was disassembled, the intestinal collagen layers removed, and treated with 100 mmol 1-ethyl-3-(3-dimethylaminopropyl) carbodiimide hydrochloride (EDC) in 50% acetone for four hours at 25° C. The material was bagged and sterilized by gamma irradiation (2.5 Mrad).

The tissue repair fabric was sutured in a 3 cm×5 cm defect in the midline of New Zealand White rabbits (4 kg) using a continuous 2-0 prolene suture. Animals were sacrificed at four weeks, ten weeks, and 16 weeks, and examined grossly, mechanically, and histologically. Gross examination showed minimal inflammation and swelling. The graft was covered with a glistening tissue layer which appeared to be continuous with the parietal peritoneum. Small blood vessels could be seen proceeding circumferentially from the periphery to the center of the patch. Mechanically the graft was stable with no reherniation observed. Histological examination revealed relatively few inflammatory cells and those that were observed were primarily near the margin of the graft (due to the presence of prolene suture material). The peritoneal surface was smooth and covered entirely by mesothelium.

Example 6

Two Layered Tissue Repair Fabric as a Pericardial Repair Patch

Two layers of porcine intestinal collagen were superimposed onto one another on a glass plate. A second plate of glass was then placed on top of the intestinal collagen layers and clamped tightly to the first plate. The apparatus was placed into a conventional type oven at 62° C. for one hour. Immediately following heating, the apparatus was placed into a 4° C. water bath for ten minutes. The apparatus was disassembled, the intestinal collagen layers removed, and treated with 10 mmol 1-ethyl-3-(3-dimethylaminopropyl) carbodiimide hydrochloride (EDC) in 50% acetone for four hours at 25° C. The material was bagged and sterilized by gamma irradiation (2.5 Mrad).

A 3×3 cm portion of New Zealand white rabbit pericardium was excised and replaced with a same size piece of tissue repair fabric (anastomosed with interrupted sutures of 7-0 prolene). Animals were sacrificed at four weeks and at 180 days, examined grossly, mechanically, and histologically. Gross examination showed minimal inflammation and swelling. Small blood vessels could be seen proceeding circumferentially from the periphery to the center to the graft. Mechanically, the graft was stable without adhesion to either the sternum or pericardial tissue. Histological examination revealed relatively few inflammatory cells and those that were observed were primarily near the margin of the graft (due to the presence of prolene suture material).

Example 7

Hernia Repair Device

A prototype device for hernia repair was developed using ICL to have a hollow inner region. The device, when completed, had a round conformation bonded at the periphery and a swollen inner region rendered swollen by the inclusion of physiological strength phosphate buffered saline. The inner region can optionally accommodate a wire coil for added rigidity or other substance for structural support or delivery of substance.

To assemble ICL multilayer sheets, 15 cm lengths of ICL were trimmed of lymphatic tags and cut down the side with the tags to form a sheet. Sheets were patted dry with Texwipes. On a clean glass plate (6"×8"), sheets were layered mucosal side down. In this case, two two-layer and two four-layer patches were constructed by layering either two or four layers of ICL on the glass plates. A second glass plate (6"×8") was placed on top of the last ICL layer and the plates were clamped together and then placed in a hydrated oven at 62° C. for one hour. Constructs were then quenched in deionized water at 4° C. for about ten minutes. The glass plates were then removed from the bath and a plate removed from each patch. The now bonded ICL layers were then smoothed out to remove any creases or bubbles. The glass plate was replaced upon the ICL layers and returned to the hydrated oven for 30–60 minutes until dry. Patches were removed from the oven and partially rehydrated by spraying with physiological strength phosphate buffered saline.

For the construction of a bi-layer construct, One bi-layer patch was removed from the glass plates and placed upon the other bi-layer patch still on the other glass plate. An annular plate ($d_{out}$=8.75 cm; $d_{in}$=6 cm) was placed upon the second patch. About 10 cc of physiological strength phosphate buffered saline was then injected through a 25 gauge needle between the two bilayer patches. A second glass plate was then placed on top of the annular plate and were then clamped together. For the construction of a four-layer construct, the same steps were followed except that two four-layer patches were used rather than two bi-layer patches. The constructs were placed in a hydrated oven at 62° C. for one hour. Constructs were then quenched in deionized water at 4° C. for about fifteen minutes. Constructs were then crosslinked in 200 mL 100 mM EDC in 50% acetone for about 18 hours and then rinsed with deionized water. The constructs were then trimmed to shape with a razor blade to the size of the outer edge of the annular plate.

Example 8

Intervertebral Disc Replacement

ICL, dense fibrillar collagen and hyaluronic acid were configured to closely approximate the anatomic structure and composition of an intervertebral disc.

Dense fibrillar collagen diskettes containing hyaluronic acid were prepared. 9 mg hyaluronic acid sodium salt derived from bovine trachea (Sigma) was dissolved in 3 mL 0.5N acetic acid. 15 mL of 5 mg/mL collagen (Antek) was added and mixed. The mixture was centrifuged to remove air bubbles. To three transwells (Costar) in a six well plate (Costar) was added 5 mL of the solution. To the area outside the transwell was added N600 PEG to cover the bottom of the membranes. The plate was maintained at 4° C. on an orbital shaker table at low speed for about 22 hours with one exchange of PEG solution after 5.5 hours. PEG solution was removed and the transwells dehydrated at 4° C./20% Rh overnight.

To assemble ICL multilayer sheets, 15 cm lengths of ICL were trimmed of lymph tags and cut down the side with the tags to form a sheet. Sheets were patted dry with Texwipes. On a clean glass plate, sheets were layered mucosal side down to five layers thick and a second glass plate was laid on top of the fifth layer. Five five-layer patches were constructed. The plates with the ICL between were clamped together and placed in a hydrated oven at 62° C. for one hour. Constructs were then quenched in RODI water at 4° C. for about ten minutes then were removed form the quench bath and stored at 4° C. until assembly of the disc.

To another glass plate, one large patch was laid. A slightly smaller patch was laid upon the first patch aligned to one edge of the larger patch. One patch was cut in half and a hole was cut in the center of each approximating the size of the DFC diskettes. With the center holes aligned, the two halves were laid upon the second patch aligned to the same edge. Three rehydrated DFC/HA diskettes were placed within the center hole. Another slightly smaller patch was laid upon the two halves containing the DFC diskettes and a larger patch laid upon the smaller patch, both aligned to the same edge. A second glass plate was placed on top of the construct. The resultant shape was that of a wedge with the thicker side being the one with the aligned edges tapering to the opposite side. The thus formed device was placed in a hydrated oven at 62° C. for one hour and then quenched in RODI water at 4° C. for about ten minutes. The device was then crosslinked in 100 mM EDC (Sigma) in 90% acetone (Baxter) for about five hours and then rinsed with three exchanges of phosphate buffered saline. The edges of the device were then trimmed with a razor blade.

Although the foregoing invention has been described in some detail by way of illustration and example for purposes of clarity and understanding, it will be obvious to one of skill in the art that certain changes and modifications may be practiced within the scope of the appended claims.

What is claimed is:

1. A prosthesis comprising two or more superimposed, bonded layers of collagenous tissue material,
   (a) wherein the layers of collagenous tissue material are sourced from a mammalian source and is the tunica submucosa of the small intestine, fascia lata, dura mater, or pericardium
   (b) wherein the layers are bonded together by heat welding from about 50° C. to about 75° C.,
   (c) wherein said prosthesis is crosslinked with a crosslinking agent that permits bioremodeling, and,
   (d) wherein said prosthesis is sterilized with peracetic acid, which, when implanted into a mammalian patient, the prosthesis undergoes controlled biodegradation occurring with adequate replacement by the patient's living cells such that the implanted prosthesis is remodeled by the living cells.

2. The prosthesis of claim 1 wherein the shape of said prosthesis is flat, tubular, or complex.

3. The prosthesis of claim 1, wherein said prosthesis is crosslinked with the crosslinking agent 1-ethyl-3-(3-dimethylaminopropyl) carbodiimide hydrochloride.

4. The prosthesis of claim 1, wherein sulfo-N-hydroxysuccinimide is added to the crosslinking agent.

5. The prosthesis of claim 1, wherein acetone is added to the crosslinking agent.

6. The prosthesis of claim 1, wherein said prosthesis is non-immunogenic.

7. The prosthesis of claim 1 wherein one or more surfaces of said prosthesis is coated with a collagenous dispersion or gel which acts as a smooth flow surface.

8. The prosthesis of claim 1 wherein said prosthesis further contains pores.

9. The prosthesis of claim 1 wherein said prosthesis is further composed of chopped collagen fibers.

10. The prosthesis of claim 1 wherein said prosthesis is further composed of collagen threads.

11. The prosthesis of claim 10 wherein said collagen threads are arranged to form a felt, a bundle, a weave or a braid.

12. The prosthesis of any of claims 9–11 wherein said collagen fibers or threads are partially or completely crosslinked.

13. The prosthesis of claim 1 wherein said prosthesis additionally contains an anticoagulant; one or more antibiotics, or one or more growth factors.

14. A method of repairing or replacing a damaged tissue comprising implanting a prosthesis in a patient comprising two or more superimposed, bonded layers of collagenous tissue material
   (a) wherein the layers of collagenous tissue material are sourced from a mammalian source and is the tunica submucosa of the small intestine, fascia lata, dura mater, or pericardium,
   (b) wherein the layers are bonded together by heat welding from about 50° C. to about 75° C.,
   (c) wherein said prosthesis is crosslinked with a crosslinking agent that permits bioremodeling, and,
   (d) wherein said prosthesis is sterilized with peracetic acid.

which, when implanted into a mammalian patient, the prosthesis undergoes controlled biodegradation occurring with adequate replacement by the patient's living cells such that the implanted prosthesis is remodeled by the living cells.

15. The prosthesis of claim 1, wherein heat for said heat welding is applied between from 60° C. to 65° C.

16. The prosthesis of claim 15, wherein heat for said heat welding is applied at 62° C.

17. The prosthesis of claim 1 wherein heat for said heat welding is applied between from about 7 minutes to about 24 hours.

18. The prosthesis of claim 17, wherein heat for said heat welding is applied for about one hour.

19. A prosthesis comprising two or more layers of collagenous tissue, (a) wherein the layers of collagenous tissue material are sourced from a mammalian source and is the tunica submucosa of the small intestine, fascia lata, dura mater, or pericardium, (b) wherein the layers are formed into a flat prosthesis, (c) wherein the layers are bonded together by heat welding from about 50° C. to about 75° C., (d) wherein said prosthesis is crosslinked with a crosslinking agent that permits bioremodeling, and, (e) wherein said prosthesis is sterilized with peracetic acid, which when said prosthesis is implanted into a mammalian patient, undergoes controlled biodegradation with adequate replacement by the patient's living cells such that the implanted prosthesis is remodeled by the living cells.

20. A prosthesis comprising two or more layers of collagenous tissue, (a) wherein the layers of collagenous tissue material are sourced from a mammalian source and is the tunica submucosa of the small intestine, fascia lata, dura mater, or pericardium, (b) wherein the layers are formed into a tubular prosthesis, (c) wherein the layers are bonded together by heat welding from about 50° C. to about 75° C., (d) wherein said prosthesis is crosslinked with a crosslinking agent that permits bioremodeling, and, (e) wherein said prosthesis is sterilized with peracetic acid, which when said prosthesis is implanted into a mammalian patient, undergoes controlled biodegradation with adequate replacement by the patient's living cells such that the implanted prosthesis is remodeled by the living cells.

21. The prosthesis of claims 18 or 19, wherein said prosthesis contains an anticoagulant, one or more antibiotics, or one or more growth factors.

22. The prosthesis of claims 18 or 19, wherein said crosslinking agent is 1-ethyl-3-(3-dimethylaminopropyl) carbodiimide hydrochloride.

23. The prosthesis of claim 18, wherein said layers are bonded at the periphery to form an inner hollow region.

24. The prosthesis of claim 19, wherein the periphery of said layers are bonded to form an inner hollow region.

* * * * *